United States Patent
Van Woudenberg

(10) Patent No.: US 7,427,921 B2
(45) Date of Patent: Sep. 23, 2008

(54) MONITORING SYSTEM CAPABLE OF GENERATING AUDIBLE MESSAGES

(75) Inventor: Roel Van Woudenberg, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 196 days.

(21) Appl. No.: 10/557,642

(22) PCT Filed: May 13, 2004

(86) PCT No.: PCT/IB2004/050685

§ 371 (c)(1),
(2), (4) Date: Nov. 17, 2005

(87) PCT Pub. No.: WO2004/104960

PCT Pub. Date: Dec. 2, 2004

(65) Prior Publication Data

US 2007/0030155 A1    Feb. 8, 2007

(30) Foreign Application Priority Data

May 21, 2003   (EP) ................... 03101444

(51) Int. Cl.
G08B 23/00    (2006.01)

(52) U.S. Cl. .................. 340/573.1; 381/110

(58) Field of Classification Search .......... 340/573.1, 340/573.4, 539.1, 539.15; 381/110
See application file for complete search history.

(56) References Cited

U.S. PATENT DOCUMENTS

| 5,774,861 | A  | * | 6/1998 | Spector .................... 381/110 |
| 6,043,747 | A  | * | 3/2000 | Altenhofen ............. 340/573.1 |
| 6,369,713 | B1 | * | 4/2002 | Halleck et al. .......... 340/573.4 |
| 7,009,520 | B2 | * | 3/2006 | Thompson .............. 340/573.1 |
| 2003/0067391 | A1 | * | 4/2003 | Fitzgerald et al. ....... 340/573.1 |

FOREIGN PATENT DOCUMENTS

WO    WO02/37474    5/2002

OTHER PUBLICATIONS

"Beamforming: A Versatile Approach to patial Filtering" by Barry D. Van Veen and Kevin M. Buckley, "IEEE ASSP Magazine" of Apr. 1988, pp. 4 to 24.
Photo of model SBC SC467 Philips Baby Monitor, 2002.

* cited by examiner

Primary Examiner—John A Tweel, Jr.

(57) ABSTRACT

A system for generating an audible message to a human includes an apparatus having an input for receiving an audio message. The audio message is stored in a memory. An output may be used for rendering the audio message. The apparatus further includes a microphone and a controller. If a sound is received via the microphone, the controller causes the stored audio message to be rendered via the output.

16 Claims, 2 Drawing Sheets

MONITORING SYSTEM CAPABLE OF GENERATING AUDIBLE MESSAGES

The invention relates to a system, in particular a baby monitor, for generating an audible message to a human.

Baby monitors typically include a baby unit and at least one parent unit. The baby unit is placed next to the bed of the baby. The unit includes a microphone. Sounds received from the baby are sent from the baby unit to the parent unit. Most baby units only send on the baby sounds if the sound level is above a certain level. The parent unit includes a speaker for rendering the sounds sent by the baby unit.

The functionality of baby monitors is increasing continuously. The Philips SBC SC467 baby monitor enables a human operator to adjust the sensitivity of the microphone. Only sounds above the chosen level are transmitted to the parent unit. The parent unit also offers the option to monitor the baby silently. In this case, the sound level of the baby is indicated visually and the speaker volume can be turned down to zero volume level. To comfort the baby the parent can talk into a microphone of the parent unit. The sound is sent to the baby unit. A speaker in the baby unit renders the parent's voice.

It is an object of the invention to provide an improved system, in particular a baby monitor, for generating an audible message to a human.

To meet the object of the invention, a system for generating an audible message to a human includes an apparatus that includes: a microphone; an input for receiving an audio message; a memory for storing a received audio message; an output for rendering an audio message; and a controller for, in response to detecting a sound received via the microphone, causing the stored audio message to be rendered via the output.

The inventor had the insight that the comforting option of the known baby monitor only works if the parent is present and able to respond to a cry from the baby. If the parents are away the voice of a baby sitter may not have the desired effect. If the parents are asleep, usually the baby has to cry sufficiently loud to wake up the parent. The parent could then use the known baby monitor to comfort the baby without having to get out of bed. However, by this time the distress of the baby may already be too high for comforting sounds to have an effect. Therefore, in the system according to the invention the apparatus that detects the sounds (e.g. of a baby) also generates the (comforting) audio message automatically. The message is recordable and stored in a memory of the apparatus. In one embodiment, the apparatus is preferably a baby unit. This may be a conventional baby unit with the described functionality being added. It may also be a stand-alone device, such as lullaby-toy. A parent can record the message and so optimally soothe the baby. The system may also be used for other functions than acting on a baby sound. In particular, the system may be used for alerting snorers or acting on sleep apnea.

In another embodiment, the apparatus includes a signal level detector for detecting a signal strength of an audio signal received via the microphone; the controller being operative to cause the rendering in response to the signal level detector detecting that the signal strength exceeds a threshold. In this way only sounds with a sufficient strength trigger the playback of the message. Preferably, the apparatus includes a user interface for enabling a human operator to determine the threshold.

In another embodiment, the apparatus includes a sound discriminator for detecting audio signals received via the microphone representative of a human sound; the controller being operative to cause the rendering in response to a trigger from the discriminator. The discriminator may be implemented in any suitable way, for example using a frequency band filter to extract frequencies that are likely to include the human sound. Also pitch detectors or speech recognizers may be used for more accurate detection. In a preferred embodiment, sounds that are sufficiently distinct from baby sounds and/or snoring can be filtered out avoiding undesired replay of the message.

In another embodiment, the input is coupled to the microphone for enabling a human operator to record the audio message. This is an effective way of recording the message. Alternatively, the message may be received from another apparatus. For example, in a baby monitor system the message may be received from the parent unit.

In another embodiment, the apparatus of the system includes a baby unit for rendering the stored audio message to a baby in response to a sound from the baby and the system further includes a parent unit; the baby unit and parent unit including respective communication means for establishing communication between the units; the controller of the baby unit being operative to cause the stored audio message to be rendered immediately after detecting the sound, and to cause an alarm signal to be sent to the parent unit only after the sound has been detected for a predetermined period; and the parent unit including an output for alerting a human; and a parent unit controller for causing the human to be alerted in response to receiving the alarm signal from the baby unit. In this way, the baby unit acts like a first line soother. If not successful within the predetermined period, the parents are still alerted. If successful, parents do not need to be woken up or do not need to take the effort to walk to the baby. The period is configurable.

In another embodiment, the sound discriminator is operative to distinguish between at least a first and second category of sound of the baby; the baby unit controller being operative to send the alarm signal to the parent unit for a sound of the first category only after the sound of the first category has been detected for a predetermined period and to send the alarm signal to the parent unit for a sound of the second category in immediate response to detecting a sound of the second category. In this way, automatic soothing occurs for the first category of sounds (e.g. a slight moaning of the baby) only followed by an alarm if the sound remains for a prolonged period. For a second category of sound requiring urgent attention (e.g. distress of the baby, sleep apnea, etc) the parent is alerted immediately.

In another embodiment, a sound that can be detected is sleep apnea. The disorder can be life-threatening, especially for babies. Sleep apnea is also serious for adults and can cause tiredness due to lack of sleep. The system according to the invention can alert the sleeper with the prerecorded message.

In another embodiment, the sound discriminator is operative to detect at least one further human sound (e.g. snoring) distinct from sleep apnea; the controller being operative to cause rendering of the audio message at distinct volume levels, where a higher volume level is used rendering the message in response to detection of sleep apnea than is used for rendering the message in response to detecting the further human sound. Since sleep apnea is a serious disorder, alarm is raised at a high level.

In another embodiment, the memory is operative to store at least one further audio message; the message to be rendered being selectable by a human and/or selected by the controller. The further message may be a pre-recorded message of a human recordable message. The operator or controller may select a distinct message as a response to a respective distinct sound detected by the apparatus. In order to keep the baby entertained a number of different sounds or recorded messages may be played in any sequence, otherwise the baby may learn that it is not the real parent soothing him, or at least lose interest and start crying again. A vast amount of pleasant sounds may be present in the device.

These and other aspects of the invention are apparent from and will be elucidated with reference to the embodiments described hereinafter.

Figure 1:
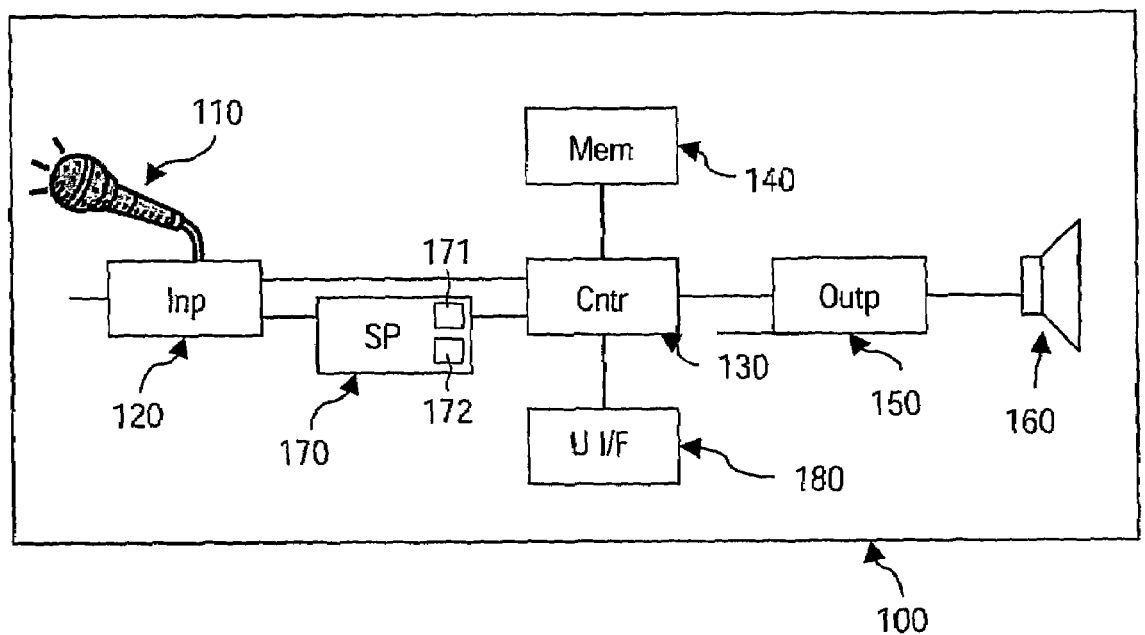
FIG. 1 shows a block diagram with a standalone apparatus.

FIG. 1 shows a block diagram of the system according to the invention. In the example of FIG. 1 the system includes one apparatus 100. The apparatus 100 may be incorporated in an existing device. For example, if the apparatus according to the invention is used for soothing a baby or child, it may be incorporated in a device that is typically present in a baby's/child's bedroom. This could be a toy, such as a lullaby toy, or an electronic device like an audio system or an alarm clock. In a preferred embodiment, the apparatus is incorporated in a baby unit of a baby monitoring system. If the apparatus is used for alerting a human in response to detecting snoring or sleep apnea, the apparatus may be incorporated in an electronic device, such as an alarm clock. The apparatus includes a microphone 110 for receiving sounds. For many applications this can be a conventional microphone as, for example, used in baby monitors. For certain applications, e.g. detecting snoring of one person and ignoring sounds of other persons in the same area, it is preferred to detect sound in a more directional way. To this end, in a preferred embodiment the microphone is a directional microphone. In an alternative embodiment, a beamformer is used. Directional microphones and beamformers are well-known. An example of a beamformer is described in "IEEE ASSP Magazine" of April 1988, pages 4 to 24. The apparatus further includes an input 120 for receiving an audio message, e.g. of a parent. In many applications the input will be connected to the microphone 110 to enable a human to speak or sing the message. The input may include an A/D converter for converting the message to a suitable digital representation. The input may also include a compressor for compressing the digital representation to reduce storage requirements. Such converters and compressors are well-known and will not be described further. Other ways of inputting the message are also possible, e.g. via a communication system to another apparatus within or outside the system or via removable storage medium, such as a solid-state memory. The received audio message is stored in a memory 140. Preferably, the memory is non-volatile, e.g. based on flash or MRAM. The apparatus also includes an output for rendering the audio message. The output may include a conventional decompressor and D/A converter. Typically the apparatus includes or is connected to a loudspeaker 160.

The apparatus further includes a controller 130 that is operable to cause the stored audio message to be rendered via the output, if a sound has been detected via the microphone. In a simple apparatus the controller may be implemented using dedicated hardware components. In a more advanced apparatus, the controller may be an embedded controller for controlling also other functions of the apparatus. The controller may even be a signal processor (such as a DSP) and be able to perform the described compression/decompression functions, beamforming and other signal processing functions as will be described below in more detail. Such a more advanced controller is operated under control of a software program. The program may be fixedly embedded in the controller. It may also be loaded from a (preferably) non-volatile memory, such as memory 140. The apparatus may include also a volatile memory, such as RAM, used during the operation of the system and erased each time the apparatus is switched off.

In an embodiment according to the invention, the apparatus includes a signal level detector 171 for detecting a signal strength of an audio signal received via the microphone 110. It may be comprised in the signal processing block 170, e.g. as a software module running on the signal processing block 170 being e.g. a digital signal processor. The detected signal strength may be based on the amplitude of a single sample. Preferably, signal strength is determined based on a consecutive sequence of samples, e.g. covering 10 msecs to 1 sec. Using a longer period decreases the chances of acting on an irrelevant sound peak. A too long period increases the risk of missing the sound of interest. Preferably, a majority voting is used on a series of those short sequences at samples taken within an interval of in total 10 secs. to two minutes. Persons skilled in the art can choose the period and/or the majority voting interval optimally for each application, depending on the characteristics of the sound of interest. The signal level detector 171 compares the signal strength to a predetermined threshold that may be stored in the memory 140. If the signal level detector detects that the signal strength exceeds a predetermined threshold it activates the rendering of the stored audio message. It will be appreciated that the function of the signal level detector 171 may be executed by the controller 130. Preferably, the apparatus includes a user interface for interaction of the apparatus with a user. Input of a user may be received via buttons or wheels or any other suitable input means, including a remote control and voice control. Output may be given via LEDs, LCD displays, or any other suitable means. Advantageously, the user can configure parameters of the signal level detector, such as the threshold level and minimum period in which the signal must be above the threshold. In this way, the apparatus can be optimally configured for a specific person and can also be configured for different applications, such as detection of baby cries, snoring detection and detection of sleep apnea. For sleep apnea, the detection may be triggered exactly the other way around. If no breathing sound is detected for a predetermined period, e.g. the microphone 110 picks up the relative silence of the bedroom during the period, or the characteristic sound patterns of sleep breathing are lost during the period, a trigger is given, as will be described in more detail below.

In an embodiment according to the invention, the apparatus includes a sound discriminator 172 for detecting audio signals received via the microphone representative of a human sound, as contrasted to non human sounds. In FIG. 1, the sound discriminator 172 is incorporated into the signal processing block 170 also used for the signal level detection. If such a human sound is detected, a trigger is given to the controller 130. In response, the controller causes the rendering of the audio message. By detecting sounds that could be from a human, other sounds can be ignored reducing the number of false renderings of the message. The sound detection can be done in many different ways. In a simple embodiment, the sound detection filters out frequencies that are most likely not generated by human mouths, e.g. using a filter that passes through frequencies in the range of 100 to 3000 Hz. In a more advanced embodiment, in particular useable for detecting baby cries, the sound detection includes detecting a pitch of the received sound. If the detected pitch falls within the range of pitches normal for babies (e.g. 300 to 900 Hz.) a trigger is issued. Pitch detection can be done in the following way. Voiced speech can be modeled as a train of Dirac impulses, representing an excitation of the vocal cords that is filtered by a filter representing the resonances in the vocal tract, the glottal source spectrum, and the radiation load spectrum. The pitch is determined by the period of the Dirac impulses. The first peak in the audio spectrum of the autocorrelation of the audio signal can be used for determining a pitch of an audio signal. Using the autocorrelation method, the pitch T is the time shift which maximizes the correlation:

$$C(k, T) = \frac{(ik^T)i(k+T)}{\|(ik)i\|\|(k+T)\|}$$

where the in-product is typically calculated over a certain number of samples S of the audio signal i(k) and the small T in the exponent of i(k) denotes a transposition. Many other ways of detecting pitch are known from speech processing applications, such as speech recognition and speech synthesis. Preferably, the sound discriminator is able to distinguish between different sounds. It may do this using speech recognition techniques that by definition are able to recognize different sounds, both voiced as well as unvoiced sounds. In particular, for baby monitoring applications, the sound discriminator is able to distinguish between at least two categories of baby sounds. Sounds may be different in many ways, e.g. being completely different sounds in frequency and sound/non-sound intervals, like snoring and sleep apnea. They may also be different in emotion, e.g. a moaning baby cry and a distressed baby cry. Such a difference in emotion may be detectable from the amplitude of the sound. WO 02/37474 describes many different emotions and ways of recognizing the emotions. These techniques may be employed in the system according to the invention to come to an accurate classification of sounds. To this end also a video camera may be used as a further input to assist in the classification.

Figure 2:
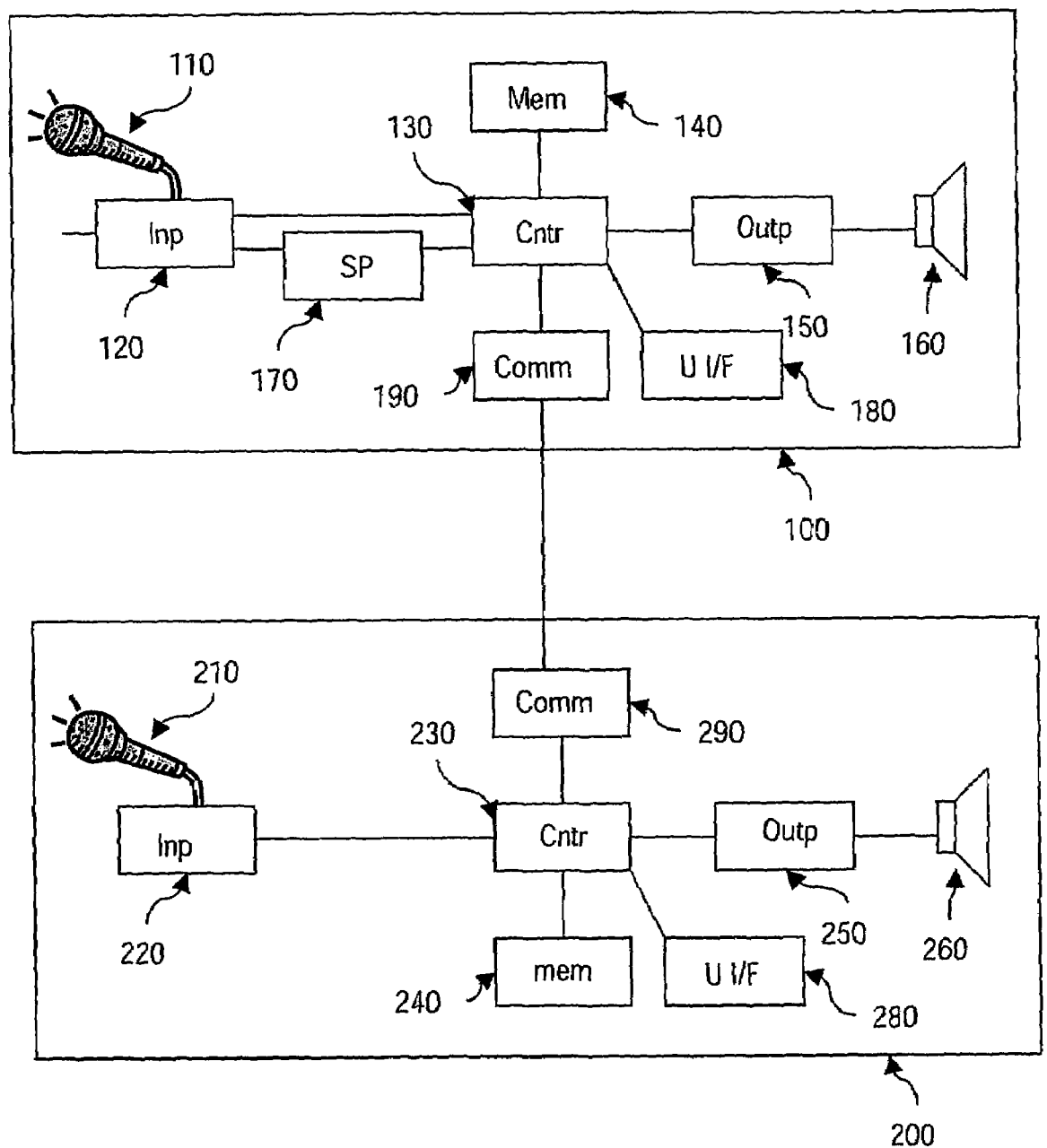
FIG. 2 shows a block diagram of a system with two communicating apparatuses, in particular a baby unit and a parent unit.

FIG. 2 shows a preferred embodiment, wherein the system in addition to the baby unit 100 of FIG. 1 also includes a parent unit 200. If so desired, the system may include multiple baby units and/or multiple parent units. The elements of the baby unit indicate with a same reference number as used for FIG. 1 perform the same function as described with reference to FIG. 1. The baby unit and parent unit include respective communication means 190, 290 for establishing communication between the units. The communication may be in any suitable form, for example as already used in baby monitoring system. Preferably, the communication is wireless. For basic operation it is sufficient if the communication is one-directional (from the baby unit to the parent unit). For more advanced applications, it is preferred to use bi-directional communication. In the preferred embodiment, the controller 130 of the baby unit immediately causes the stored audio message to be rendered locally if it detects a sound. It sends an alarm signal to the parent unit via the communication means 190 only after the sound has been detected for a predetermined period. A human operator may configure the period in which the baby unit does not alert the parent unit. The parameter may be stored in the memory 140. The configuration may take place via the user interface 180 of the baby unit. It may also take place via a user interface 280 of the parent unit, if two-way communication is possible. The alarm signal may be sent in any suitable form. Advantageously, the baby unit simply passes on the sound that it receives (e.g. the baby cries). So, it does not pass on the sound as long as the period has not expired. Passing on the baby sounds after expiry of the period enables the parent to accurately assess the distress of the baby. The sound of the baby may be passed on in an analogue or digital form. The alarm signal may also be a digital code, such as a short digital message, to trigger the parent unit. The parent unit includes an output 250 for alerting a human. Preferably, the output is connected to a speaker 260. If the alarm is received via the communication means 290 as a digital trigger signal (e.g. message), the parent unit may issue any specific alarm signal, e.g. produce an alarm ring tone or produce a flashing light. Such signal may be issued via a user interface 280 of the parent unit. The controller 230 of the parent unit is responsible for causing the human to be alerted in response to receiving the alarm signal from the baby unit. The controller may be any suitable microcontroller or processor. It may come with embedded software or the software may be loaded from a (preferably non-volatile) memory, such as a memory 240. The parent unit may also include a microphone (210) or be connected to it. Via this microphone a parent may be able to talk directly to the baby, input the message to be stored in the baby unit, etc. The microphone may be connected to an input 220 that may include an A/D converter and audio compressor. The parent unit may also be incorporated in another device, such as a television, or portable device like a mobile phone, or personal digital assistance assistant (PDA).

As described above, the sound discriminator 172 may be able to distinguish between at least a first and second category of sound of the baby. For a baby monitoring system, the first category of sound includes any baby sound that does not require immediate attention of a parent (or caretaker), e.g. moaning sounds, and sounds with a low distress factor. For sounds of this category, the baby unit controller 130 immediately renders the stored message, but only after the sound has been detected for the predetermined period it sends the alarm signal to the parent unit. In this way, the system automatically tries to sooth the baby without alarming the parent (yet). Sounds of the second category are sounds that may require immediate attention. Such sounds may include baby cries with high distress (e.g. high volume) or sleep apnea. The controller 130 sends an alarm signal to the parent unit immediately when a sound of the second category is detected. It will be appreciated that more categories can be defined, each with a respective response at the local apparatus and/or remote apparatus.

As described above, the sound discriminator is preferably operative to detect sleep apnea. This can be useful for babies, where sleep apnea is a major cause of cot-deaths, as well as for adults. During sleep, the body is relatively at rest. The heartbeat and body temperature drop. This process is completely automatic. People with sleep apnea have trouble with the breathing process during their sleep. Sometimes they stop breathing for a minute and wake up in panic. Sleep apnea can be characterized as repeated periods of total or partly blocking of the air passage longer than 10 seconds, causing oxygen deprivation. The disorder can be life-threatening, especially for babies. Often babies have difficulties during their sleep. Difficulties with breathing are among these. Fortunately, most babies wake up automatically. Cot-deaths occur mainly in the first two years of a baby. Particularly during this period it is important that parents can intervene if breathing stops too long. Children or adults with sleep apnea wake up all the time and consequently don't get enough rest during the night. They are very tired during the day. Most of the times, the body turns into an emergency-state when deprived of oxygen for a while. For older children and adults it is preferred that the system alerts them in time before the oxygen-deprivation occurs. A minor disturbance of the person involved may be enough to restart the breathing process without fully waking the person. Since apnea is serious, it is preferred that if breathing is not restarted quickly, the audio message is rendered at a high volume level. As described the audio message may be rendered to the person itself, or in the case of the baby monitoring system, to the parents through the parent unit. The baby unit may then also still issue the message to awaken the baby in case the parents are not present or asleep too fast (or the parent unit is switched off). The high volume level is higher than used for rendering an audio message for other sounds.

One of the other sounds that the system can detect in a preferred embodiment is human snoring. Snoring can be described as breathing during sleep with a rough hoarse noise due to vibration of the uvula and soft palate. In particular for snoring, it is desired that only the snorer is stimulated to move a bit so that the snoring stops. To achieve this, the audio message is rendered at a level lower than usually used for waking a human, using a conventional loudspeaker. In such a case, the connection between the output 150 and the loudspeaker 160 may be a conventional wired connection. It is also possible to use a loudspeaker that can be detached from the apparatus. This can be achieved by using a longer wire. Advantageously, a wireless connection is used between the apparatus and the loudspeaker. This is particularly useful if the apparatus is used for alerting a snorer. In such an application the loudspeaker may be a loudspeaker that can be put on or under the pillow or at least very near to the snorer so that no other people in the room are alerted. Such loudspeakers in itself are known and typically used by people who listen to music or a book while resting on bed. In a preferred embodiment, the loudspeaker is an ear-mounted loudspeaker as is well-known from loudspeakers for people with a hearing disorder. If the loudspeaker can be positioned very near the person involved the volume level can be chosen such that the person involved is alerted, but that no other people are disturbed. As an alternative to or in addition to alerting the human using sound, also other stimuli may be used. For alerting a snorer or person with sleep apnea, preferably a vibrator is used. Vibrators are well-known for example from mobile phones.

The description of the system given above focuses on using one audio message for alerting a human. It will be appreciated that the memory 140 may be able to store several audio messages of which at least one is recordable. The other messages may be recordable or prerecorded. Using a system with multiple messages, the message to be rendered may be selectable by a human via the user interface. In a simple embodiment, only one message can be rendered by the system, where the human can select which one. In a more advanced embodiment, the system is able to render different messages for different events. For example, a different message for snoring than for sleep apnea. In such a system the user can preferably select for each event a message to be rendered. Alternatively, the controller selects the message most suited for the event, e.g. a soothing message if the person should continue sleeping and an alarming message if the person should wake up (or partly awake up). Preferably, the user can also select a volume level for rendering for each event or each message. The settings selected by the user can be stored in the memory 140 and applied by the controller during rendering.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verbs "comprise" and "include" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for generating an audible message for a monitored human; the system including an apparatus including:
   a microphone;
   an input for receiving different audio messages;
   a memory for storing the received different audio messages;
   an output for rendering the different audio messages; and
   a controller for, in response to detecting a sound received via the microphone, causing the stored different audio messages to be rendered via the output in different sequences to reduce a likelihood that the monitored human may learn that the rendered different messages are stored.

2. The system as claimed in claim 1, wherein the apparatus includes a signal level detector for detecting a signal strength of an audio signal received via the microphone; the controller being operative to cause the rendering in response to the signal level detector detecting that the signal strength exceeds a predetermined threshold.

3. The system as claimed in claim 1, wherein the apparatus includes a sound discriminator for detecting audio signals, received via the microphone, representative of a human sound; the controller being operative to cause the rendering in response to a trigger from the discriminator.

4. The system as claimed in claim 1, wherein the input is coupled to the microphone for enabling a human operator to record the audio message.

5. The system as claimed in claim 1, wherein the apparatus includes a baby unit for rendering the stored audio message to a baby in response to a sound from the baby.

6. A system for generating an audible message for a human; the system including an apparatus including:
   a microphone;
   an input for receiving an audio message;
   a memory for storing the received audio message;
   a baby unit for rendering the stored audio message to a baby;
   a controller for, in response to detecting a sound from the baby received via the microphone, causing the stored audio message to be rendered via the baby unit; and
   a parent unit; the baby unit and parent unit including respective communication means for establishing communication between the baby unit and parent unit; the controller being operative to cause the stored audio message to be rendered immediately after detecting the sound, and to cause an alarm signal to be sent to the parent unit only after the sound has been detected for a predetermined period; and the parent unit including an output for alerting a human; and a parent unit controller for causing the human to be alerted in response to receiving the alarm signal from the baby unit.

7. The system as claimed in claim 6, wherein the system includes at least one user interface for enabling a human operator to configure the predetermined period.

8. A system for generating an audible message for a human; the system including an apparatus including:
- a microphone;
- an input for receiving an audio message;
- a memory for storing the received audio message;
- a baby unit for rendering the stored audio message to a baby;
- a controller for, in response to detecting a sound received via the microphone, causing the stored audio message to be rendered via the output; and
- a sound discriminator for detecting audio signals, received via the microphone, representative of a human sound; the controller being operative to cause the rendering in response to a trigger from the discriminator;
- wherein the sound discriminator is operative to distinguish between at least a first and second category of sound of the baby; the controller being operative to send an alarm signal to a parent unit for a sound of the first category only after the sound of the first category has been detected for a predetermined period and to send the alarm signal to the parent unit for a sound of the second category in immediate response to detecting a sound of the second category.

9. The system as claimed in claim 3, wherein the sound discriminator is operative to detect sleep apnea by detecting at least one of silence.

10. The system for generating an audible message for a human; the system including an apparatus including:
- a microphone;
- an input for receiving an audio message;
- a memory if or storing the received audio message;
- a baby unit for rendering the stored audio message to a baby;
- a controller for, in response to detecting a sound received via the microphone, causing the stored audio message to be rendered via the output; and
- a sound discriminator for detecting audio signals, received via the microphone, representative of a human sound; the controller being operative to cause the rendering in response to a trigger from the discriminator;
- wherein the sound discriminator is operative to detect at least one further human sound distinct from sleep apnea; and wherein the controller is operative to cause rendering of the stored audio message at distinct volume levels, where a higher volume level is used rendering the stored audio message in response to detection of the sleep apnea than is used for rendering the stored audio message in response to detecting the further human sound.

11. The system as claimed in claim 10, wherein the further human sound is human snoring.

12. The system as claimed in claim 1, wherein the memory is operative to store at least one further audio message; the message to be rendered being selectable by a human and/or selected by the controller.

13. The system as claimed in claim 3, wherein the sound discriminator is operative to detect sleep apnea by detecting loss of characteristic sound patterns of sleep breathing.

14. The system as claimed in claim 1 wherein, in response to detecting silence, the controller is configured to render one of the stored different audio messages at higher volume than other stored different audio messages to awaken the monitored human.

15. The system as claimed in claim 1 wherein, in response to detecting snoring by the monitored human, the controller is configured to render one of the stored different audio messages at lower volume than other stored different audio messages to prevent awakening the monitored human.

16. The system as claimed in claim 15, further comprising a vibrator configured to be activated upon detection of the snoring.

* * * * *